United States Patent
Hester et al.

(10) Patent No.: US 7,867,279 B2
(45) Date of Patent: Jan. 11, 2011

(54) INTERVERTEBRAL DISC PROSTHESIS

(75) Inventors: Douglas L. Hester, Raynham, MA (US); Paul S. Maguire, Hope Valley, RI (US); Alexander D. Grinberg, Newton, MA (US)

(73) Assignee: DePuy Spine, Inc., Raynham, MA (US)

( * ) Notice: Subject to any disclaimer, the term of this patent is extended or adjusted under 35 U.S.C. 154(b) by 115 days.

(21) Appl. No.: 11/337,388

(22) Filed: Jan. 23, 2006

(65) Prior Publication Data

US 2007/0173936 A1     Jul. 26, 2007

(51) Int. Cl.
*A61F 2/44* (2006.01)

(52) U.S. Cl. .................... 623/17.14; 623/17.15

(58) Field of Classification Search .......... 606/61, 606/246, 279; 623/17.11–17.16
See application file for complete search history.

(56) References Cited

U.S. PATENT DOCUMENTS

| | | | |
|---|---|---|---|
| 4,759,766 A | 7/1988 | Buettner-Janz et al. | |
| 4,997,432 A | 3/1991 | Keller | |
| 5,236,460 A | 8/1993 | Barber | |
| 5,258,031 A | 11/1993 | Salib et al. | |
| 5,314,477 A * | 5/1994 | Marnay | 623/17.15 |
| 5,360,430 A | 11/1994 | Lin | |
| 5,370,697 A | 12/1994 | Baumgartner | |
| 5,401,269 A | 3/1995 | Buttner-Janz et al. | |
| 5,425,773 A | 6/1995 | Boyd et al. | |
| 5,458,641 A | 10/1995 | Ramirez Jimenez | |
| 5,507,816 A | 4/1996 | Bullivant | |
| 5,556,431 A | 9/1996 | Buttner-Janz | |
| 5,562,738 A | 10/1996 | Boyd et al. | |
| 5,676,701 A | 10/1997 | Yuan et al. | |
| 5,683,465 A | 11/1997 | Shinn et al. | |

(Continued)

FOREIGN PATENT DOCUMENTS

EP     0 535 973     7/1993

(Continued)

OTHER PUBLICATIONS

Krag et al., "An Internal Fixator for Posterior Application to Short Segments of the Thoracic, Lumbar, or Lumbosacral Spine," *Clinical Orthopaedics and Related Research*, vol. 203, pp. 75-98, Feb. 1986 (24 pages).

(Continued)

*Primary Examiner*—Thomas C Barrett
*Assistant Examiner*—Andrew Yang
(74) *Attorney, Agent, or Firm*—Maginot, Moore & Beck (57) ABSTRACT

An intervertebral disc prosthesis comprises a first plate including a socket and a second plate comprising a recess. A core is sandwiched between the socket and the recess. The core includes a domed surface and a plug portion. The first plate is configured to rotate upon the domed surface of the core. The second plate is substantially fixed to the core, with the plug portion engaging the recess. The core may be press-fit into the second plate during assembly of the intervertebral disc prosthesis. The first plate and second plate both include tabs that define notches, wherein the notches are configured to engage prongs of a disc insertion tool. Teeth provided on the first plate and the second plate assist in fixing the first plate and the second plate to the vertebral bodies.

16 Claims, 6 Drawing Sheets

U.S. PATENT DOCUMENTS

| | | | |
|---|---|---|---|
| 5,782,830 A | 7/1998 | Farris | |
| 5,782,832 A | 7/1998 | Larsen et al. | |
| 5,851,207 A | 12/1998 | Cesarone | |
| 5,895,428 A | 4/1999 | Berry | |
| 5,899,941 A | 5/1999 | Nishijima et al. | |
| 5,989,291 A | 11/1999 | Ralph et al. | |
| 6,019,792 A | 2/2000 | Cauthen | |
| 6,063,121 A | 5/2000 | Xavier et al. | |
| 6,066,174 A | 5/2000 | Farris | |
| 6,113,605 A | 9/2000 | Storer | |
| 6,113,637 A | 9/2000 | Gill et al. | |
| 6,146,421 A | 11/2000 | Gordon et al. | |
| 6,159,215 A | 12/2000 | Urbahns et al. | |
| 6,179,874 B1 | 1/2001 | Cauthen | |
| 6,228,118 B1 | 5/2001 | Gordon | |
| 6,296,665 B1 | 10/2001 | Strnad et al. | |
| 6,319,257 B1 | 11/2001 | Carignan et al. | |
| 6,368,350 B1 | 4/2002 | Erickson et al. | |
| 6,375,682 B1 | 4/2002 | Fleischmann et al. | |
| 6,395,030 B1 | 5/2002 | Songer et al. | |
| 6,395,034 B1 | 5/2002 | Suddaby | |
| 6,416,551 B1 | 7/2002 | Keller | |
| 6,440,142 B1 | 8/2002 | Ralph et al. | |
| 6,440,168 B1 | 8/2002 | Cauthen | |
| 6,517,580 B1 | 2/2003 | Ramadan et al. | |
| 6,520,996 B1 | 2/2003 | Manasas et al. | |
| 6,524,312 B2 | 2/2003 | Landry et al. | |
| 6,527,804 B1 | 3/2003 | Gauchet et al. | |
| 6,540,785 B1 | 4/2003 | Gill et al. | |
| 6,562,074 B2 | 5/2003 | Gerbec et al. | |
| 6,579,320 B1 | 6/2003 | Gauchet et al. | |
| 6,599,294 B2 | 7/2003 | Fuss et al. | |
| 6,610,093 B1 | 8/2003 | Pisharodi | |
| 6,616,671 B2 | 9/2003 | Landry et al. | |
| 6,652,534 B2 | 11/2003 | Zucherman et al. | |
| 6,660,006 B2 | 12/2003 | Markworth et al. | |
| 6,663,637 B2 | 12/2003 | Dixon et al. | |
| 6,682,561 B2 | 1/2004 | Songer et al. | |
| 6,682,562 B2 | 1/2004 | Viart et al. | |
| 6,740,118 B2 | 5/2004 | Eisermann et al. | |
| 6,793,678 B2 | 9/2004 | Hawkins | |
| 2002/0035400 A1 | 3/2002 | Bryan et al. | |
| 2002/0111679 A1 | 8/2002 | Zucherman et al. | |
| 2002/0111681 A1 | 8/2002 | Ralph et al. | |
| 2002/0111682 A1 | 8/2002 | Ralph et al. | |
| 2002/0111683 A1 | 8/2002 | Ralph et al. | |
| 2002/0111684 A1 | 8/2002 | Ralph et al. | |
| 2002/0111685 A1 | 8/2002 | Ralph et al. | |
| 2002/0111686 A1 | 8/2002 | Ralph et al. | |
| 2002/0111687 A1 | 8/2002 | Ralph et al. | |
| 2002/0128714 A1 | 9/2002 | Manasas et al. | |
| 2002/0128715 A1 | 9/2002 | Bryan et al. | |
| 2002/0143399 A1 | 10/2002 | Sutcliffe | |
| 2002/0161366 A1 | 10/2002 | Robie et al. | |
| 2002/0161375 A1 | 10/2002 | Ralph et al. | |
| 2002/0169508 A1 | 11/2002 | Songer et al. | |
| 2003/0033016 A1 | 2/2003 | Dees, Jr. | |
| 2003/0040802 A1 | 2/2003 | Errico et al. | |
| 2003/0065395 A1 | 4/2003 | Ralph et al. | |
| 2003/0069586 A1 | 4/2003 | Errico et al. | |
| 2003/0069643 A1 | 4/2003 | Ralph et al. | |
| 2003/0074066 A1 | 4/2003 | Errico et al. | |
| 2003/0074067 A1 | 4/2003 | Errico et al. | |
| 2003/0074068 A1 | 4/2003 | Errico et al. | |
| 2003/0074069 A1 | 4/2003 | Errico et al. | |
| 2003/0074070 A1 | 4/2003 | Errico et al. | |
| 2003/0074071 A1 | 4/2003 | Errico et al. | |
| 2003/0074072 A1 | 4/2003 | Errico et al. | |
| 2003/0074073 A1 | 4/2003 | Errico et al. | |
| 2003/0074074 A1 | 4/2003 | Errico et al. | |
| 2003/0074076 A1 | 4/2003 | Ferree et al. | |
| 2003/0078664 A1 | 4/2003 | Ralph et al. | |
| 2003/0078665 A1 | 4/2003 | Ralph et al. | |
| 2003/0078666 A1 | 4/2003 | Ralph et al. | |
| 2003/0083747 A1 | 5/2003 | Winterbottom et al. | |
| 2003/0135277 A1 | 7/2003 | Bryan et al. | |
| 2003/0135278 A1 | 7/2003 | Eckman | |
| 2003/0149482 A1 | 8/2003 | Michelson | |
| 2003/0176923 A1 | 9/2003 | Keller et al. | |
| 2003/0191534 A1 | 10/2003 | Viart et al. | |
| 2003/0204261 A1 | 10/2003 | Eisermann et al. | |
| 2003/0233148 A1 | 12/2003 | Ferree | |
| 2004/0002761 A1 | 1/2004 | Rogers et al. | |
| 2004/0010316 A1 | 1/2004 | William et al. | |
| 2004/0024462 A1 | 2/2004 | Ferree et al. | |
| 2004/0030390 A1 | 2/2004 | Ferree | |
| 2004/0039448 A1 | 2/2004 | Pisharodi | |
| 2004/0044410 A1 | 3/2004 | Ferree et al. | |
| 2004/0068318 A1 | 4/2004 | Coates et al. | |
| 2004/0073311 A1 | 4/2004 | Ferree | |
| 2004/0073313 A1 | 4/2004 | Link et al. | |
| 2004/0083000 A1 | 4/2004 | Keller et al. | |
| 2004/0111160 A1 | 6/2004 | Evans et al. | |
| 2004/0117022 A1 * | 6/2004 | Marnay et al. | 623/17.16 |
| 2004/0138750 A1 | 7/2004 | Mitchell | |
| 2004/0138753 A1 | 7/2004 | Ferree | |
| 2004/0153157 A1 | 8/2004 | Keller | |
| 2004/0167626 A1 * | 8/2004 | Geremakis et al. | 623/17.15 |
| 2004/0243240 A1 | 12/2004 | Beaurain et al. | |
| 2005/0033437 A1 | 2/2005 | Bao et al. | |
| 2005/0234553 A1 | 10/2005 | Gordon | |
| 2006/0095133 A1 * | 5/2006 | Eisermann et al. | 623/17.14 |
| 2006/0111783 A1 * | 5/2006 | Aflatoon et al. | 623/17.14 |
| 2006/0116768 A1 * | 6/2006 | Krueger et al. | 623/17.14 |
| 2006/0149371 A1 * | 7/2006 | Marik et al. | 623/17.11 |
| 2006/0241760 A1 * | 10/2006 | Randall et al. | 623/17.11 |

FOREIGN PATENT DOCUMENTS

| | | | |
|---|---|---|---|
| EP | 0 560 140 | 9/1993 | |
| EP | 0699426 | 3/1996 | |
| EP | 0 955 021 | 11/1999 | |
| EP | 1 344 506 | 9/2003 | |
| EP | 1 344 507 | 9/2003 | |
| EP | 1 344 508 | 9/2003 | |
| FR | 2 636 227 | 9/1988 | |
| WO | WO 91/13598 | 9/1991 | |
| WO | WO 99/05995 | 2/1999 | |
| WO | 9965412 | 12/1999 | |
| WO | WO 02/080818 | 10/2002 | |
| WO | WO 03/075803 | 9/2003 | |
| WO | 03084449 | 10/2003 | |
| WO | 03090650 | 11/2003 | |
| WO | WO 2004/016217 | * 2/2004 | 623/17.13 |

OTHER PUBLICATIONS

Kostuik, John P., "Intervertebral Disc Replacement," *Clinical Orthopaedics and Related Research*, No. 337, pp. 27-41, Apr. 1997 (15 pages).

Karaikovic et al., "Possible Complications of Anterior Perforation of the Vertebral Body Using Cervical Pedical Screws," *Journal of Spinal Disorders & Techniques*, vol. 15, No. 1, pp. 75-78, 2002 (4 pages).

McAfee et al., "Cervical Disc Replacement—Porous Coated Motion Prosthesis," *Spine*, vol. 28, No. 20S, pp. S176-S185, 2003 (10 pages).

Jöllenbeck et al., "Early Experiences with Cervical Disc Prostheses," *Zentralblatt für Neurochiurgie* (*Central European Neurosurgery*), vol. 65, No. 3, pp. 123-127, 2004 (5 pages).

Meier et al., Experiences with Six Different Intervertebral Disc Spacers for Spondylodesis of the Cervical Spine, Orthopäde, vol. 33, Issue 11, pp. 1290-1299, Nov. 2004 (11 pages with English language Abstract).

Johnson et al. "Sagittal alignment and the Bryan cervical artificial disc," *Neurosurgical Focus*, vol. 17, No. 6, pp. 1-4, Dec. 2004 (4 pages).

Kotani et al., "Multidirectional flexibility analysis of cervical artificial disc reconstruction: in vitro human cadaveric spine model," *Journal Neurosurgery Spine*, vol. 2, pp. 188-194, Feb. 2005 (7 pages).

Buttner-Janz, K et al., Biomechanics of the SB Charite lumbar intervertebral disc endoprosthesis; International Orthopaedics; 1989; pp. 173-176; vol. 13, Issue 3; Humboldt University; Germany (4 pages).

Cunningham, BW et al., General principles of total disc replacement arthroplasty: seventeen cases in a nonhuman primate model; 2003; pp. 118-124; vol. 28, Issue 20; Lippincott Wiliams & Wilkins; US (7 pages).

Enker P, et al., Artificial Disc Replacement, Preliminary Report with a 3-Year Minimum Follow-up; 1993, pp. 1061-1070, vol. 18, No. 8, J.B. Lippincott Company, US (10 pages).

One (1) page English abstract of the following German article: Buttner-Janz K et al., An alternative treatment strategy in lumbar intervertebral disk damage using an SB Charite modular type intervertebral disk endoprosthesis; Z Orthop Ihre Grenzgeb; Jan.-Feb. 1987; 125(1): 1-6.

\* cited by examiner

INTERVERTEBRAL DISC PROSTHESIS

BACKGROUND

This invention relates to the field of prosthetics, and more particularly, to an intervertebral disc prosthesis designed to replace a damaged intervertebral disc.

The human spine consists of twenty-four small bones known as vertebrae, or "vertebral bodies," that protect the spinal cord and provide stability to the torso. The vertebrae are arranged in a column and stacked vertically upon each other. Between each vertebra is a fibrous bundle of tissue called an intervertebral disc. These intervertebral discs act as a cushion to the spinal column by absorbing the shock and pressure associated with everyday movement. They also prevent the vertebrae from rubbing against each other.

Each intervertebral disc comprises two distinct regions. A firm outer region maintains the shape of the intervertebral disc. An inner region provides a soft spongy tissue that enables the disc to function as a shock absorber. Over time, the normal aging process causes the intervertebral discs to degenerate, diminishing their water content and thereby reducing their ability to properly absorb the impact associated with spinal movements. Diminished water content in the intervertebral discs may also cause the vertebrae to move closer together. Tears and scar tissue can weaken the discs, resulting in injury. When the discs wear out or are otherwise injured, they do not function normally and may cause pain and limit activity. Such injury may result in a condition known as degenerative disc disease.

The condition of degenerative disc disease can potentially be relieved by a surgical procedure called artificial disc replacement. In this procedure, the damaged intervertebral disc is replaced by a prosthetic disc. One well known intervertebral prosthetic disc is produced by DePuy Spine, Inc. of Raynaham, Mass. and is sold under the trademark CHARITE®.

Although current intervertebral disc prosthetic devices have enjoyed success, it would be desirable to add additional desirable features to the prosthetic device. For example, for it would be desirable to provide a three-piece prosthetic disc design including a core sandwiched between a superior plate and an inferior plate where the core is secured to the inferior plate using a simple press-fit arrangement and the core is restricted from rotating relative to the inferior plate. Additionally, it would be advantageous to design the intervertebral disc prosthesis wherein the prosthesis may be more easily grasped and retained by an insertion tool in order to facilitate implantation of the prosthesis in the patient.

SUMMARY

An intervertebral disc prosthesis comprises a first plate including a socket and a second plate comprising a recess. A core is sandwiched between the socket and the recess. The first plate is configured to rotate upon the core. The core is fixed to the second plate.

The core generally includes an upper portion in the form of a dome-shaped bearing surface and a lower portion in the form of a cylindrical plug portion. The socket of the first plate provides an articulating surface configured to engage the dome-shaped bearing surface of the core, thus allowing the first plate to rotate upon the core. The plug portion of the core is configured to engage the recess of the second plate, substantially fixing the core to the second plate. The recess is provided on the second plate within a collar. The recess is defined by a circular wall and a flat floor. The plug of the core is configured to be press-fit into the recess by a friction fit or a snap fit. In one embodiment, the second plate includes at least one indentation in the recess.

In one embodiment, the first plate and second plate include notches configured to receive retention arms of a disc insertion tool. In particular, the notches are provided in the anterior portions of the first plate and the second plate. Tabs are also provided in the anterior portions of the first plate and the second plate which at least partially define the notches. The notches and tabs are designed to allow prongs of a disc insertion tool to fit into the notches and grasp the tabs during insertion of the prosthesis in a patient.

In one embodiment, the first plate and the second plate of the intervertebral disc prosthesis are tapered from an anterior edge to a posterior edge such that they collectively define a lordotic angle of 7°, with 3.5° contributed from each plate.

In addition to the above, the intervertebral disc prosthesis comprises at least one tooth positioned on a face of the first plate and at least one tooth positioned on a face of the second plate. The teeth are configured to secure the intervertebral disc prosthesis to the vertebral bodies.

DESCRIPTION

General Structure

Figure 1:
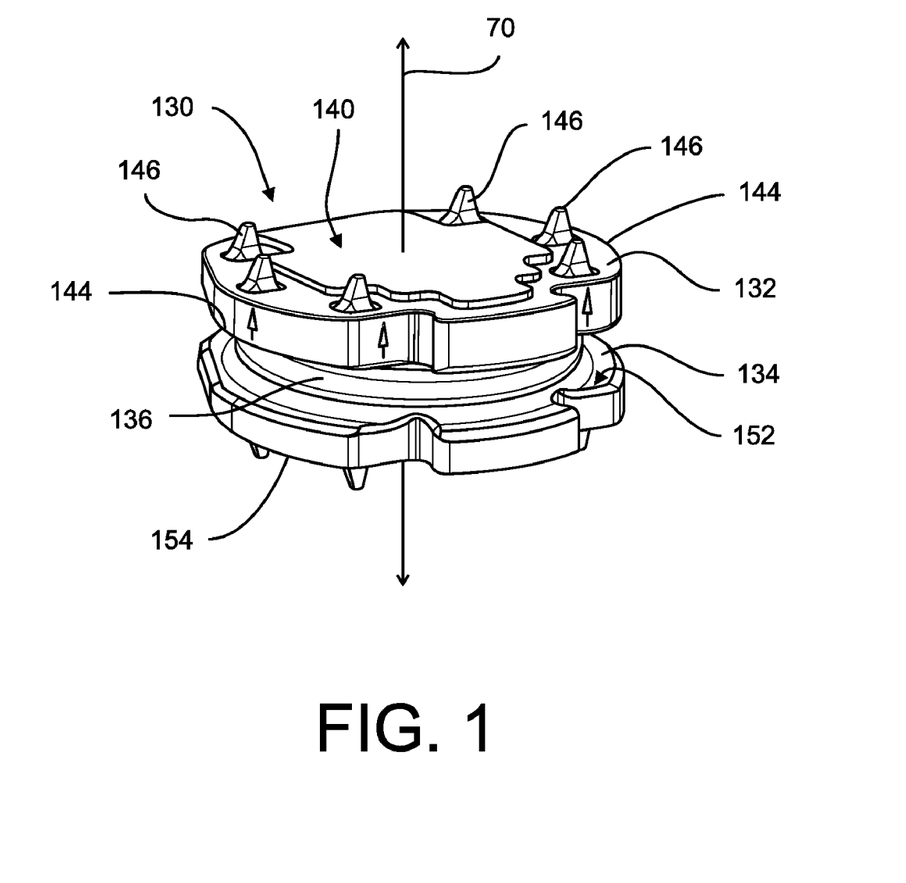
FIG. 1 shows a perspective view of an intervertebral disc prosthesis including a superior plate and a inferior plate separated by a core.
Figure 2:
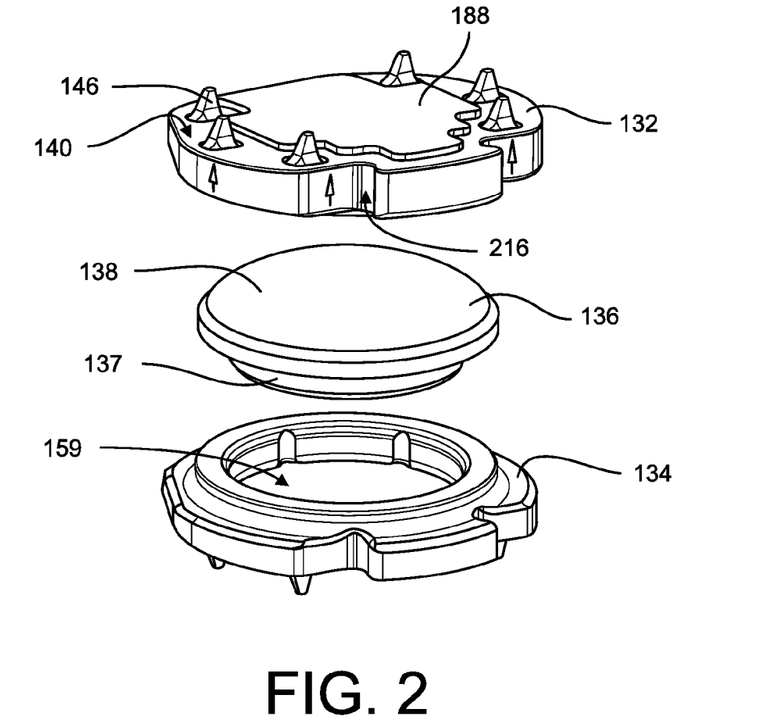
FIG. 2 shows an exploded isometric view of the intervertebral disc prosthesis of FIG. 1.
Figure 5:
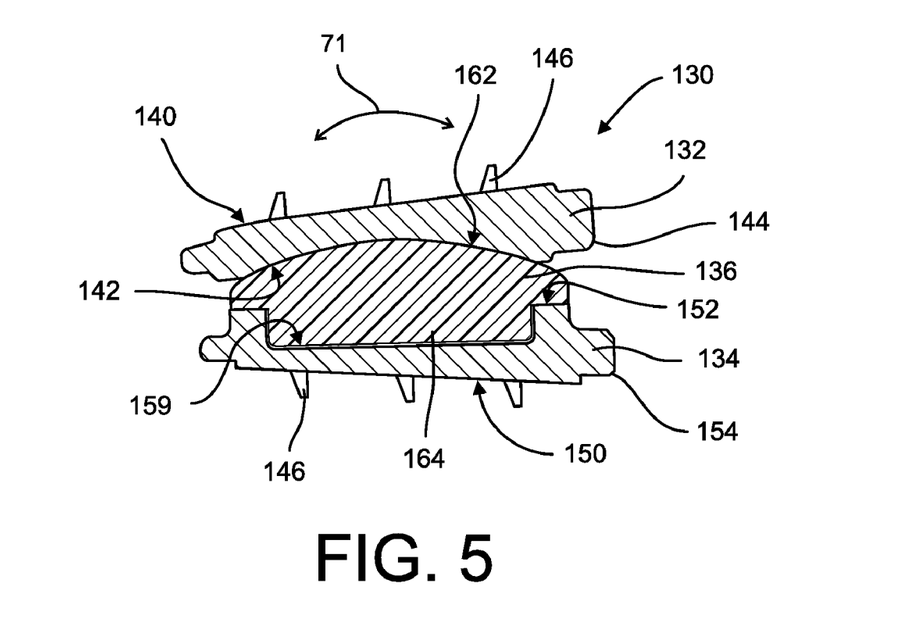
FIG. 5 shows a side cross-sectional view of the intervertebral disc prosthesis of FIG. 1 with the superior plate rotated to display flexion.

With general reference to FIGS. 1 and 5, an intervertebral disc prosthesis 130 comprises a superior plate 132, an inferior plate 134, and a core 136. The core 136 is sandwiched between the superior plate 132 and the inferior plate 134. The superior plate 132 rides upon the core 136 and is operable to rotate relative to the core, including torsional rotation about vertical axis 70 of FIG. 1, flexion/extension rotation as indicated by arrow 71 of FIG. 5, and lateral bending rotation (not shown). The core is press-fit into a recess 159 in the inferior plate 134 and is substantially fixed relative to the inferior plate 134.

The superior plate 132 serves as a first endplate for the prosthetic device 130. The superior plate 132 is comprised of metal. In particular, the superior plate 132 is comprised of titanium alloy. However, as discussed in further detail below, the superior plate may be comprised of numerous other materials such as cobalt chromium. The superior plate 132 comprises an upper surface 140 on one side and a lower surface 142 on the other side. An outer perimeter edge 144 defines the "footprint" shape of the superior plate 132.

Figure 3:
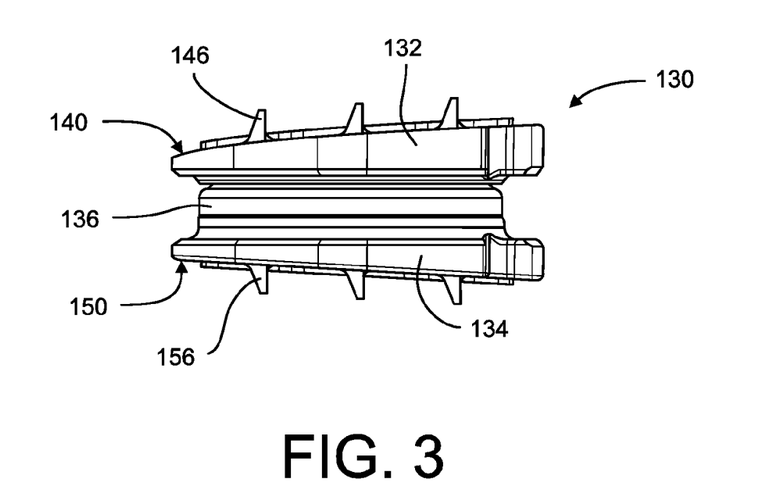
FIG. 3 shows a side elevational view of the assembled intervertebral disc prosthesis of FIG. 2.

The upper surface 140 of the superior plate 132 is designed for engagement with a vertebral surface of a patient. To this end, teeth 146 are included on the upper surface 140 of the superior plate 132. The teeth 146 are designed to penetrate into the vertebral surface, helping to secure the superior plate 132 to the vertebral surface. As shown in FIG. 3, the teeth 146 extend from the upper surface of the superior endplate 132. The teeth 146 are generally pyramidal in shape with a rectangular base positioned on the outer surface 140 of the endplate.

The lower surface 142 of the superior plate 132 defines an inner concave surface 149. This inner concave surface 149 serves as a socket for a ball and socket arrangement, with the ball portion of the ball and socket arrangement found on the core 136.

Figure 4:
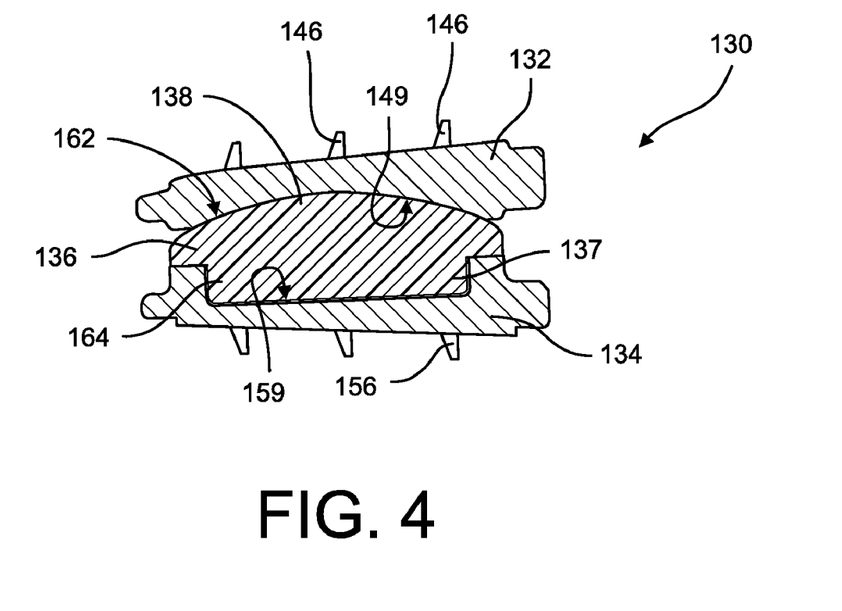
FIG. 4 shows a cross-sectional view of the intervertebral disc prosthesis through line A-A of FIG. 6.

The inferior plate is generally shown in FIGS. 3-5. Like the superior plate, the inferior plate 134 is also made of a medical grade titanium alloy, or other material such as cobalt chromium. The inferior plate 134 includes a generally flat inferior surface 150 outlined by an outer perimeter edge 154. A plurality of teeth 156 extend from the inferior surface 150. The teeth 156 are designed to help secure the inferior plate 134 to a vertebral surface. Like the teeth 146 of the superior plate, the teeth 156 of the inferior plate are generally pyramidal in shape with a rectangular base positioned on the lower outer surface 150 of the inferior plate 134. As explained in further detail below, the upper inner surface 152 of the inferior plate 134 includes a recess 159 which is configured to receive the core 136 such that the core 136 is fixed to the inferior plate 134.

The prosthesis core 136 is sandwiched between the superior plate 132 and the inferior plate 134. The prosthesis core 136 is comprised of a plastic material having a high slip factor, such as ultra-high molecular weight polyethylene, which allows the superior endplate 132 to slide easily on the core. The prosthesis core 136 includes an upper spherical portion and surface 162, and a lower cylindrical portion 164.

When the prosthesis 130 is assembled, the concave surface 149 of the superior plate 132 and the upper spherical surface 162 of the core 136 engage one another and form articular surfaces. At the same time, the cylindrical portion 164 of the core engages the recess 159 of the inferior plate 34, thus securing the core 136 to the inferior plate 134.

Endplate Footprint

Figure 6:
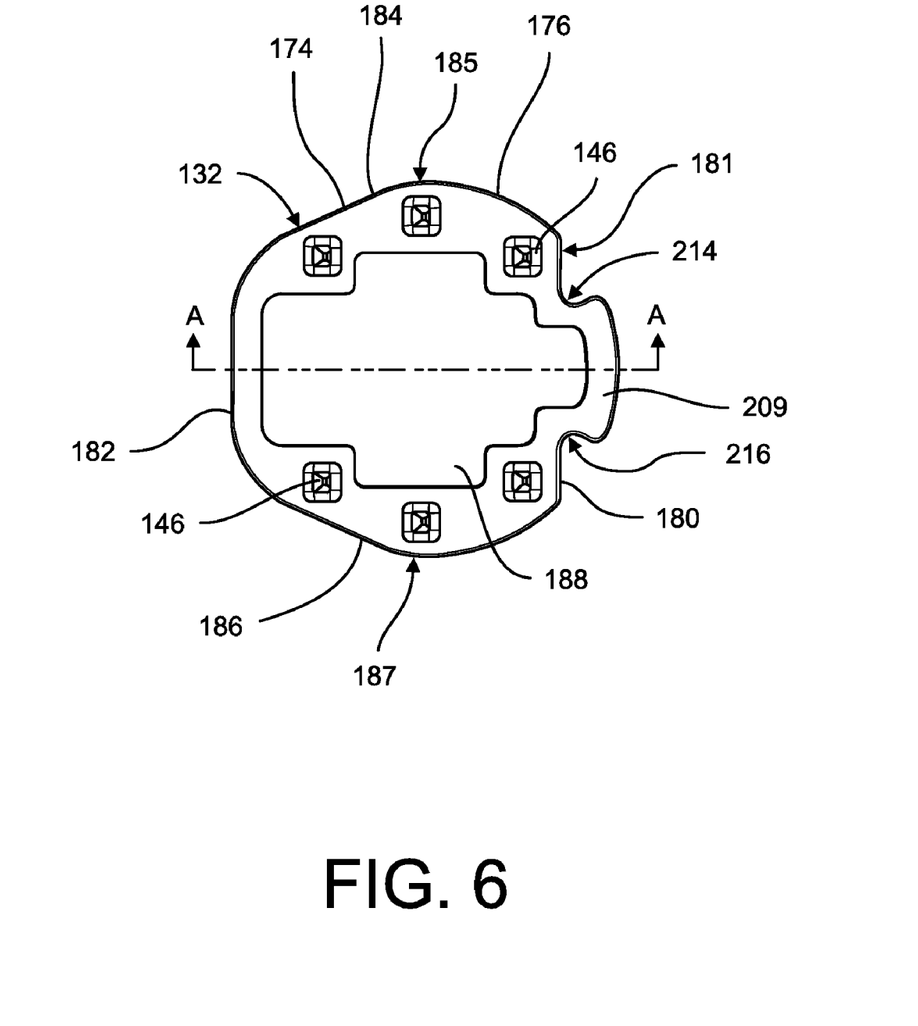
FIG. 6 shows a top view of the intervertebral disc prosthesis of FIG. 1.
Figure 7:
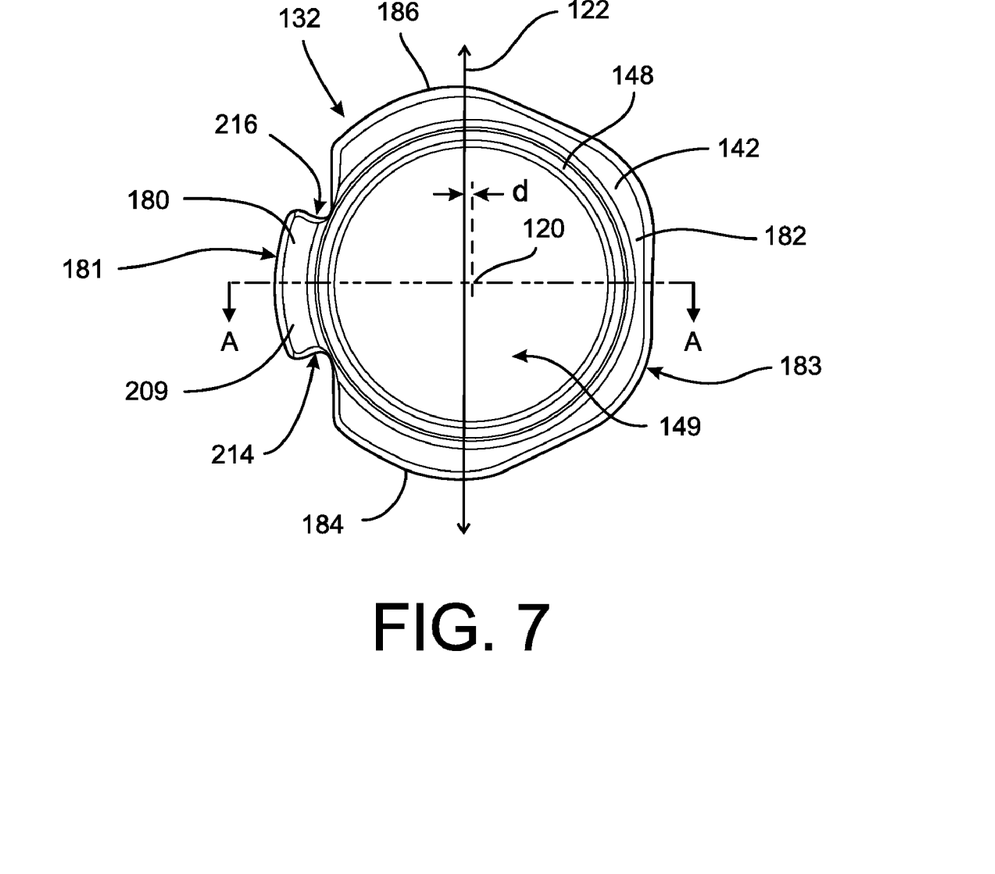
FIG. 7 shows a bottom view of the superior plate of the intervertebral disc prosthesis of FIG. 1.

As shown in FIGS. 6 and 7, the superior plate 132 is configured to include an anterior side 180, a posterior side 182, a left side 184, and a right side 186. The left side 184 of the superior endplate 132 is generally symmetric to the right side 186 of the plate 132. The left edge 185 is curved and defines a posterior bevel 174 and an anterior bevel 176. The anterior side 180 of the endplate 132 includes a tab 209 extending from an otherwise flat anterior edge 181. The tab 209 and anterior edge 181 in general define a left notch 214 and a right notch 216 formed in the anterior side of the endplate. As explained in further detail below, these notches 214, 216 are designed to receive a disc insertion tool to facilitate implantation of the disc in a patient.

The inferior plate 134 includes similar features as those described in the preceding paragraph, as the "footprints" of the endplates 132 and 134 are symmetrical. The above-described endplate footprint allows the endplate to substantially conform to the cervical vertebral body of the patient. In particular, the endplate footprint covers a substantial portion of the cervical vertebral body, thus providing a substantial amount of surface area for connection and bony in-growth between the endplate and the vertebral body. This in-growth may be facilitated by a porous bony in-growth coating on the endplates. The coating on the superior endplate is generally placed as a coating pad 188 found on the surface of the endplate that faces the vertebral body. In one embodiment, the coating comprises plasma sprayed titanium and hydroxyapatite (HA). In other embodiments, the coating comprises calcium phosphate, a matrix of cross-linked collagen fibers coated with HA (such as that sold under the trademark Healos®), or other osteoconductive materials as are known in the art. Such osteoconductive materials and/or coatings generally provide a porous substrate capable of accommodating bone growth. Osteoconductive coatings may be applied by various processes as are known in the art, including physical packing, brushing, spraying, chemical vapor deposition, physical vapor deposition, electrochemical deposition, or other methods as are known in the art.

Endplate Interior Surfaces

As discussed above, and as shown in FIGS. 7 and 8, the lower surface 142 of the superior endplate 132 includes a concave dome-shaped bearing surface 149. The concave bearing surface 149 may also be referred to as an articulating surface 149. The concave bearing surface 149 provides a socket designed to engage the dome-shaped core 136, thus allowing the superior endplate 132 to rotate upon the core 136.

Figure 10:
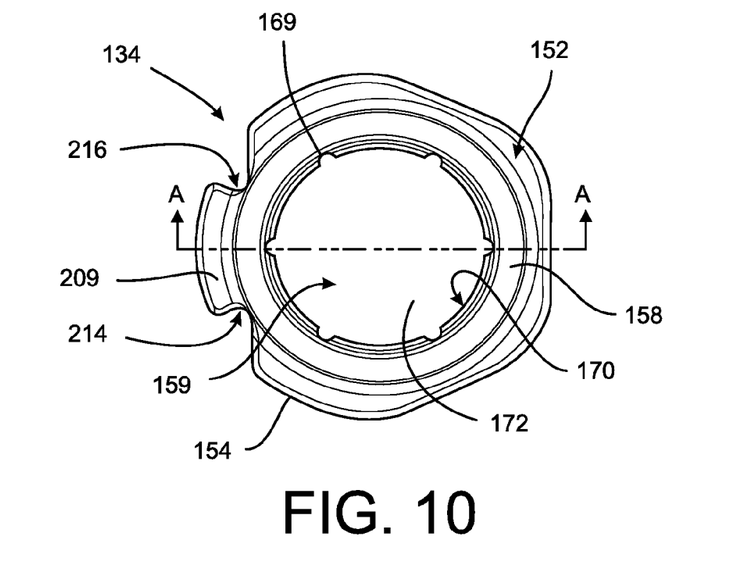
FIG. 10 shows a top view of the inferior plate of the intervertebral disc prosthesis of FIG. 1.
Figure 11:
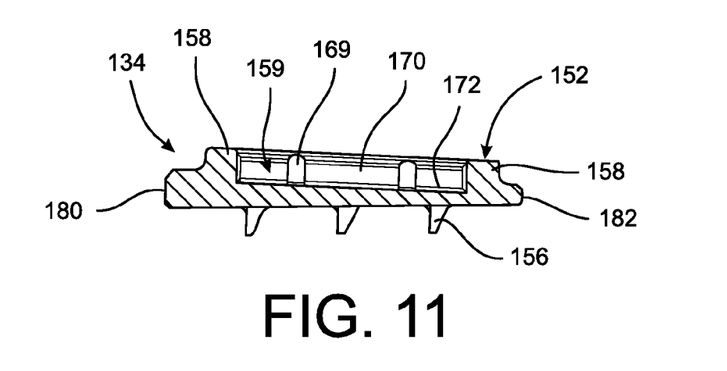
FIG. 11 shows a cross-sectional view of the inferior plate through line A-A of FIG. 10.

Although the footprint of the inferior endplate 134 is symmetric to the footprint of the superior endplate 132, the upper interior surface 152 of the inferior endplate 134 is distinct from the lower surface 142 of the superior endplate 132. As shown in FIGS. 10 and 11, a circular recess 159 is provided within a collar 158 in the upper surface 152 of the inferior endplate 134. The circular recess 159 includes a circular wall 170 that extends down from the collar 158 of the inferior plate 134. The circular wall 170 ends in a flat floor 172 that defines the lower portion of the recess 159. A plurality of semi-cylindrical cavities 169 or other indentations are formed in the circular wall. These indentations 169 are provided to prevent rotation of the core 136 and provide for conduction of ethylene oxide (ETO) during the sterilization process. In particular, the indentations 169 allow for slight migration of the core 136 into the indentations 169 to prevent rotation. Also, during the sterilization process, gaseous ETO can penetrate into the recess 159 of the inferior plate 134 through the indentations 169.

Core

Figure 9:
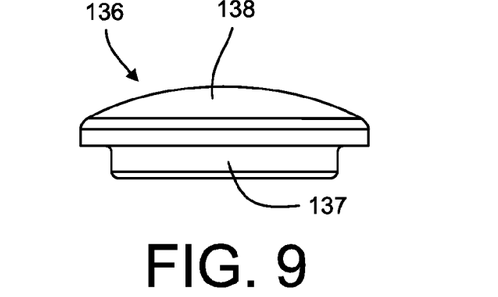
FIG. 9 shows a side view of the core of the intervertebral disc prosthesis of FIG. 1.

The core 136 is comprised of an ultra high molecular weight polyethylene. As shown in FIG. 9, the core 136 includes a cylindrical-shaped base portion 137 and a convex dome-shaped top portion 138. The dome-shaped top portion provides an articular surface designed to engage the socket 149 of the superior plate, thus allowing the superior plate 132 to rotate/pivot upon the core 136. The base portion 137 of the core 136 is a plug 137 designed to fit within the recess 159 of the inferior plate 134. In particular, the base portion 137 is designed to be press-fit within the recess 159 of the inferior plate 134, thus securing the core 136 to the inferior plate 134. As used herein, the term "press-fit" refers to an arrangement where the core is secured to the plate by placing the core upon the plate and forcing the core in a direction directly toward the plate. Examples of press-fit arrangements include friction-fit arrangements and snap-fit arrangements. A friction-fit arrangement is disclosed herein, as the plug 137 is slightly larger than the recess 159, resulting in slight deformation of the plug 137 and frictional engagement between the plug and the recess when the plug is press-fit into the recess. When the core 136 is secured to the inferior plate 134 it is substantially fixed in place upon the inferior endplate such that the core will not move with respect to the inferior endplate during normal operation of the prosthesis when it is implanted in a patient.

With reference to FIG. 4, when the prosthesis 130 is assembled, the base portion 137 of the core 136 fits within and is secured to the recess 159 of the inferior plate 132. At the same time, the socket 149 of the superior plate 132 engages the dome-shaped portion 138 of the core 136, allowing the superior plate 132 to pivot upon the core 136, while the inferior plate 134 is fixed to the core 136.

Posterior Center of Rotation

Figure 8:
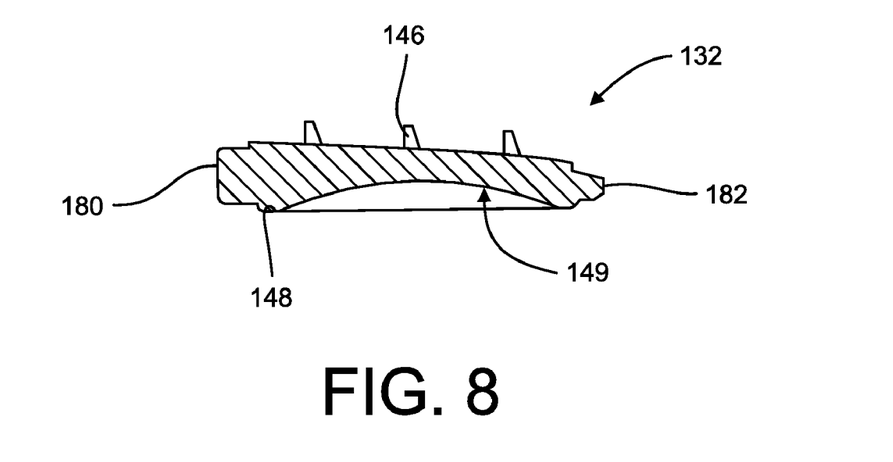
FIG. 8 shows a cross-sectional view of the superior plate through line A-A of FIG. 7.

As mentioned above, FIGS. 7 and 8 show the lower surface 142 of the superior plate 132 of one embodiment of the intervertebral disc prosthesis 130. As shown in FIGS. 7 and 8, a concave dome-shaped bearing surface 149 is formed in the lower surface 142 of the superior plate. The concave bearing surface 149 provides a socket for the core 136 of the prosthesis. The concave bearing surface 149 defines a center-of-rotation for the superior plate 132. The position of the center of rotation is shown in FIG. 7 by a "+" 120. Also shown in FIG. 7 is a lateral midline 122 extending laterally across the plate from the left side 184 to the right side 186. The lateral midline 122 is a line located directly between the furthermost anterior edge and the furthermost posterior edge of the endplate 132.

As shown in FIG. 7, the radial collar 148 is centered upon the plate such that it is slightly closer to the posterior edge 183 than the anterior edge 181 of the plate. As a result, the center of rotation 120 of the superior plate 132 is positioned to the posterior of the lateral midline 122. In particular, the center of rotation 120 is located a distance "d" behind the lateral midline 122. In a preferred embodiment, the center of rotation is 0.25 mm posterior to the lateral midline. This posterior center of rotation arrangement mimics the true anatomy of healthy vertebral bodies and intervertebral discs.

Insertion Features

With reference again to FIGS. 8 and 11, the endplates 132 and 134 of the prosthesis are designed with several features that allow the prosthesis 130 to be more easily inserted into the intervertebral space. For example, the height of each endplate 132, 134 is tapered such that the posterior side 182 of the endplate has a smaller height than the anterior side 180 of the endplate. In this embodiment, the endplate becomes gradually thicker from the posterior side 182 to the anterior side 180 of the endplate. This allows the endplate to incorporate a lordotic angle in the sagittal plane of the prosthesis. For example, if each endplate incorporates a 3.5° angle from anterior to posterior, the intervertebral prosthesis as a whole will incorporate a 7° lordotic angle in the sagittal plane. Endplates incorporating such a lordotic angle may be desirable for certain patients.

The endplates of the intervertebral disc prosthesis include handle portions which are designed to assist with insertion of the prosthetic device in the intervertebral space. In one embodiment, the handle portions are dovetails provided on the anterior portion of the endplates. As best seen in FIGS. 1, 6, 7, and 10, the dovetails may be provided by the notches 214, 216 in the anterior edge 181 of the endplate 132. In this embodiment, the notches 214, 216 are designed to accept the prongs of a disc insertion tool. In particular, the prongs of a disc insertion tool may be inserted into the notches 214, 216, allowing the prongs to grasp the tab 209 extending from the anterior edge 181. By grasping the tab 209, the insertion tool is able to hold the endplate and encourage the endplate toward the intervertebral space during the implantation procedure.

Alternative Materials

As discussed above, the metal endplates 132, 134 are comprised of a titanium alloy and the core is comprised of an ultra high molecular weight polyethylene. The use of titanium in the endplates is advantageous because titanium is MRI compatible. In many prior art prosthetic devices, the endplates were comprised of a cobalt chromium, which is not MRI compatible. However, physicians often desire an MRI image rather than an x-ray image of an implanted prosthesis. Thus, endplates 132 and 134 comprised of titanium alloy are advantageous to allow MRI imaging of the prosthesis device. The use of titanium alloy also allows visualization of the anatomic structures behind the prosthesis. Other MRI compatible materials that could be used for the endplates include ceramic, polycarbonate-polyurethane (PCPU), polyetheretherketone (PEEK), or composites thereof.

In addition to alternative materials that make the intervertebral prosthesis MRI compatible, other materials may be advantageous to the surgeon, depending upon the desired outcome for the patient. For example, a ceramic core could be used for excellent wear performance in the youngest patients. A PCPU core could be used to offer shock-absorbing capabilities for more active patients.

Furthermore, the prosthesis core may be injection molded in order to manufacture a single component core having properties that vary throughout the component in an advantageous manner. For example, the core may be manufactured in a manner such that the core provides a soft bearing surface on the exterior and a rigid support skeleton on the inside. Alternate core materials could include PEEK or titanium with a wear-improving coating, in addition to ultra-high molecular weight polyethylene (UHMWPE). Alternate combinations of interest from a wear perspective include metal matrix composites (MMC) with cobalt chromium or MMC with ceramic. Example ceramics include synthetic ruby, zirconia, alumina, zirconia toughened alumina (ZTA), Y-TZP, silicon nitride, or combinations thereof. In one embodiment, a one-piece polycarbonate-polyurethane (PCPU) core could be produced by multi-shot or insert injection molding a relatively rigid central frame with a relatively soft outer bearing surface (e.g., shore 55D frame and shore 80A bearing). In another embodiment, layered sintering of MMC to a similar metal results in a MMC bearing surface applied to a metal frame.

After selecting and receiving the proper endplates 132 and 134 and core 136 for a particular patient, the surgeon assembles the intervertebral prosthesis 130 by sandwiching the core between the endplates. In particular, the plug 137 portion of the core 136 is press-fit into the recess of the inferior plate 134. Thereafter, the superior plate 132 is placed upon the dome-shaped top portion 138 of the core 136 such that the superior plate is free-floating upon the core. Once assembled the prosthesis may be implanted in the patient as a complete unit using an insertion tool.

Although the present invention has been described with respect to certain preferred embodiments, it will be appreciated by those of skill in the art that other implementations and adaptations are possible. For example, although the prosthetic discs shown herein are cervical discs, the features disclosed herein could also be applied to other types of prosthetic discs, such as lumbar discs. Moreover, there are advantages to individual advancements described herein that may be obtained without incorporating other aspects described

What is claimed is:

1. An intervertebral disc prosthesis comprising:
   a) a first plate including a socket;
   b) a second plate having a first coupling member that includes an inner wall structure that defines a recess; and
   c) a core positioned between the socket and the recess, the core comprising a domed surface engaging the socket of the first plate and a plug engaging the second plate, wherein the core has a second coupling member that includes a substantially cylindrically-shaped outer wall structure that defines the plug, and further the second coupling member is positioned within the recess so that the substantially cylindrically-shaped outer wall structure contacts the inner wall structure in a friction fit manner,
   wherein the second plate further includes a rim positioned completely around an opening defined by the recess, and the core further includes a ledge positioned in contact with the rim.

2. The intervertebral disc prosthesis of claim 1 wherein the first plate and second plate are both tapered from an anterior edge to a posterior edge defining a lordotic angle.

3. The intervertebral disc of claim 1 wherein the first plate and the second plate both include a tab that define notches in the first plate and the second plate, wherein the notches are configured to receive prongs of a disc insertion tool.

4. An intervertebral disc prosthesis comprising:
   a) a first plate;
   b) a second plate having a first coupling member that includes an inner wall structure that defines a recess; and
   c) a core positioned between the first plate and the second plate, wherein the core has a second coupling member that includes a substantially cylindrically-shaped outer wall structure, and further the second coupling member is positioned within the recess so that the substantially cylindrically-shaped outer wall structure contacts the inner wall structure in a friction fit manner, and further wherein the first plate is configured to rotate upon the core and the second plate is substantially fixed to the core due to physical interaction between the substantially cylindrically-shaped outer wall structure and the inner wall structure,
   wherein the first plate comprises a socket and the core is positioned between the socket of the first plate and the recess of the second plate, and
   wherein the second plate includes at least one indentation in the recess of the second plate.

5. An intervertebral disc prosthesis comprising:
   a) a first plate;
   b) a second plate having a first coupling member that includes an inner wall structure that defines a recess; and
   c) a core positioned between the first plate and the second plate, wherein the core has a second coupling member that includes a substantially cylindrically-shaped outer wall structure, and further the second coupling member is positioned within the recess so that the substantially cylindrically-shaped outer wall structure contacts the inner wall structure in a friction fit manner, and further wherein the first plate is configured to rotate upon the core and the second plate is substantially fixed to the core due to physical interaction between the substantially cylindrically-shaped outer wall structure and the inner wall structure,
   wherein the first plate comprises a socket and the core is positioned between the socket of the first plate and the recess of the second plate, and
   wherein the second plate further includes a rim positioned completely around an opening defined by the recess, and the core further includes a ledge positioned in contact with the rim.

6. The intervertebral disc prosthesis of claim 5 wherein the second plate further includes a flat floor located within the recess.

7. The intervertebral disc prosthesis of claim 5 wherein the core comprises a dome-shaped bearing surface and a plug portion, wherein the dome-shaped bearing surface of the core is configured to rotatably engage the socket of the first plate and the plug portion of the core is substantially fixed in the recess of the second plate.

8. An intervertebral disc prosthesis comprising:
   a) a first plate;
   b) a second plate having a first coupling member that includes an inner wall structure that defines a recess; and
   c) a core positioned between the first plate and the second plate, wherein the core has a second coupling member that includes a substantially cylindrically-shaped outer wall structure, and further the second coupling member is positioned within the recess so that the substantially cylindrically-shaped outer wall structure contacts the inner wall structure in a friction fit manner, and further wherein the first plate is configured to rotate upon the core and the second plate is substantially fixed to the core due to physical interaction between the substantially cylindrically-shaped outer wall structure and the inner wall structure,
   wherein the inner wall structure of the second plate further defines a plurality of anti-rotation cavities.

9. An intervertebral disc prosthesis, comprising:
   a) a first prosthesis component having (i) a first vertebra facing surface, and (ii) a first bearing surface;
   b) a second prosthesis component having (i) a second vertebra facing surface, and (ii) a first coupling member that includes an inner wall structure that defines a recess, and
   c) an intermediate prosthesis component interposed between said first prosthesis component and said second prosthesis component, said intermediate prosthesis component having (i) a second bearing surface positioned in contact with said first bearing surface of said first prosthesis component, and (ii) a second coupling member that includes a substantially cylindrically-shaped outer wall structure, wherein the second coupling member is positioned within the recess so that the substantially cylindrically-shaped outer wall structure contacts the inner wall structure in a friction fit manner,
   wherein said second prosthesis component further includes a rim positioned completely around an opening defined by the recess, and the intermediate prosthesis component further includes a ledge positioned in contact with the rim.

10. The intervertebral disc prosthesis of claim 9, wherein:
said second coupling member includes a plug, and
said plug is received within said recess in a friction fit manner.

11. An intervertebral disc prosthesis, comprising:
   a) a first prosthesis component having (i) a first vertebra facing surface, and (ii) a first bearing surface;
   b) a second prosthesis component having (i) a second vertebra facing surface, and (ii) a first coupling member that includes an inner wall structure that defines a recess, and c) an intermediate prosthesis component interposed between said first prosthesis component and said second prosthesis component, said intermediate prosthesis component having (i) a second bearing surface positioned in contact with said first bearing surface of said first prosthesis component, and (ii) a second coupling member that includes a substantially cylindrically-shaped outer wall structure, wherein the second coupling member is positioned within the recess so that the substantially cylindrically-shaped outer wall structure contacts the inner wall structure in a friction fit manner, wherein said second coupling member includes a plug, wherein said plug is received within said recess in a friction fit manner, and wherein the first coupling member includes at least one indentation in the recess.

12. The intervertebral disc prosthesis of claim 11 wherein the first bearing surface is defined by a socket and the second bearing surface is a dome-shaped surface.

13. The intervertebral disc prosthesis of claim 11 wherein the first prosthesis component includes notches configured to receive retention arms of a disc insertion tool.

14. The intervertebral disc of claim 13 wherein the anterior portion of the first prosthesis component further comprises a tab positioned between the notches.

15. The intervertebral disc prosthesis of claim 11 further comprising a plurality of teeth extending from the first prosthesis component and the second prosthesis component.

16. The intervertebral disc prosthesis of claim 11 wherein the first prosthesis component is tapered from an anterior edge to a posterior edge such that the first plate defines half of a lordotic angle.

* * * * *